United States Patent [19]
Friess et al.

[11] Patent Number: 5,695,749
[45] Date of Patent: Dec. 9, 1997

[54] COMPOSITION CONTAINING CHOLESTYRAMINE AND METHOD OF PRODUCING THE SAME

[75] Inventors: Stefan Friess; Harald Heckenmüller, both of Hamburg, Germany

[73] Assignee: Astra Aktiebolag, Sodertalje, Sweden

[21] Appl. No.: 244,453

[22] PCT Filed: Mar. 31, 1994

[86] PCT No.: PCT/SE94/00291

§ 371 Date: May 25, 1994

§ 102(e) Date: May 25, 1994

[87] PCT Pub. No.: WO94/25039

PCT Pub. Date: Nov. 10, 1994

[30] Foreign Application Priority Data

Apr. 29, 1993 [DE] Germany .................. 43 14 583.3

[51] Int. Cl.$^6$ .................. A61K 47/00; A61K 31/785
[52] U.S. Cl. .................. 424/78.16; 424/439; 424/440
[58] Field of Search .................. 424/78.1, 78.16, 424/439, 440

[56] References Cited

U.S. PATENT DOCUMENTS 5,026,555 6/1991 Schulz .................. 424/499
5,167,965 12/1992 Killeen .................. 424/439

FOREIGN PATENT DOCUMENTS 0347014 12/1989 European Pat. Off. .
0492235 7/1992 European Pat. Off. .

Primary Examiner—Peter F. Kulkosky
Attorney, Agent, or Firm—White & Case

[57] ABSTRACT

Cholestyramine and starch containing, oil-free compositions with excellent organoleptic features are obtained by mixing cholestyramine and grain starch in a weight ratio of 1:1.8 to 2.9 with the addition of grain bran as a filler and optionally an aroma stuff with 10 to 35% by weight of water (calc. on the starting materials) into a homogenous moist mass, forming of the mass through extrusion into a string, whereby the temperature is 105°–180° C. (measured in the mass in the extrusion head) and the pressure is 30–70 bars (measured in the extrusion head), and subsequently drying at a temperature above 100° C. to a remaining humidity of $\leq 3.5\%$ by weight, whereby the extruded material before or after the drying is divided into bars or is grinded into a powder.

12 Claims, No Drawings

COMPOSITION CONTAINING CHOLESTYRAMINE AND METHOD OF PRODUCING THE SAME

The invention relates to a method of producing oil-free compositions containing cholestyramine and starch, esp. in the form of bars for the immediate consumption by hypercholesterolemia patients.

Cholestyramine is the international free name (INN of WHO) for the chloride of a styrene-divinyl benzene-copolymerisate containing quaternary ammonium groups. Cholestyramine is effective as ion exchanger for binding of gallic acids and at hypercholesterolemia as lipid-lowering agent. In the last mentioned use quite large dosages have to be used, which might be as high as between 4 and 16 g for each separate delivery and up to 32 g daily. This is a problem because cholestyramine is present in the form of very fine, water-insoluble ion-exchange particles. When eating this in suspended or solid form a fishy smell and taste occurs and moreover an unpleasant sandy taste remains in the mouth thereafter, which sometimes is also called "drifting sand effect". Therefor it is difficult to get patients to take in cholestyramine preparations on a regular basis over a prolonged time in the required high doses.

The most varying attempts have already been made to transfer cholestyramine into a more patient-friendly form, which should be easy to use, i.e. could be eaten directly, and tasty. Among others, suspensions (e.g. in the form of fruit juices), powder, bakery products and bars (for example in the form of sweet nougat or chocolate bars) have been developed.

The cholestyramine compositions according to DE-A-38 08 191 are present in the form of an aquous suspension with fixed viscosity.

The EP-A-347 014 describes cholestyramine containing bakery products, which are manufactured by baking for 20 minutes at about 150°–180° C. from a dough, which, besides water contains a cooking oil, a mono- or polysaccharide, flavorings as well as cholestyramine.

From the EP-A-492 235 are previously known non-baked cholestyramine products with a moisture content of <11%. These products contain cholestyramine, cereals such as flour or bran, sugar, flavorings, binding agents based on starch as well as optionally cooking oil. The working is performed in such a way that the mixture is not baked at temperatures of 150° C. or above, but instead is dried at about 70° C. under reduced pressure over a long time of about 16 to 48 hours, until the desired low moisture content has been achieved.

None of the suggestions known sofar has led to a cholestyramine product in solid form, which fulfill the above mentioned claims regarding smell and taste, having a simple composition and being apt to be manufactured only with the aid of technologies at disposal. The object of the invention is to solve these problems.

Surprisingly it has been found that in view of nutritional physiology and also in view of taste and smell in all aspects satisfactory cholestyramine products are obtained in solid form, when the recipe as well as the manufacturing conditions are selected in a certain way and are adjusted to each other.

Thus, the object of the invention is a method for manufacturing cholestyramine and starch containing compositions free of oil, preferably in the form of bars, especially for the immediate intake by hypercholesterolemia patients, which is characterized in that cholestyramine and grain starch in a weight ratio of 1:1.8 to 2.9, preferably 1:2.2 to 2.7, with the addition of grain bran as filling agent and optionally a flavoring with 10–35% by weight of water (relative to the starting materials) are mixed into a homogeneous moist mass, which mass is processed by extrusion into a string, whereby the temperature (measured in the mass in the extrusion head) is 105°–180° C. and the pressure (measured in the extrusion head) is 30–70 bar, and in that subsequently a drying is performed at a temperature above 100° C. to a remaining moisture content of $\leq 3.5\%$ by weight, whereby the extruded material preferably before or after the drying step is divided into bars or is ground into a powder.

By "bars" within the scope of the present invention is meant disc- or blockshaped articles. The dimensions are chosen so that a bar contains the single dose to be administered of cholestyramine. With a thickness of 1–12 mm the width may be e.g. 20–50 mm and the length 100–160 mm.

Alternatively the extruded material can be grinded into a powder (particle size preferably <2 mm) and in this form be added to e.g. milk, water, juice containing compote or other drinks, yogurt and the like.

The organoleptic characteristics of special advantage are obtained with a surprisingly simply built recipe. Normal additives such as oils or fats, fermentative agents and taste masking polymers or gelating agents are not needed. The optional addition of flavorings is substantially performed in order to achieve different trends in taste and less for pasting the taste and smell of the products per se.

According to a preferred embodiment starch and bran from the same grain, that is for example wheat starch and wheat bran, are used in a recipe. The content of bran (referring to the starting materials) is usually less than 10% by weight, preferably up to 7.5% by weight. In case flavorings are used, e.g. special dry flavorings of bread type, the application on the bar might be performed right at the end of the manufacturing process after the drying of the bar.

Wheat, rice and corn starch are especially well suited. Regarding the bran used this is preferably wheat or rice bran. Then the bran as such might be stabilized by the addition of starch.

Especially preferred compositions consist of 30% by weight of cholestyramine, 65% by weight of wheat starch and 5% by weight of wheat bran and of 25% by weight of cholestyramine, 67.5% by weight of wheat starch and 7.5% by weight of wheat bran, respectively. Optionally, to this is also added the dry flavoring.

Further, for the advantages achieved according to the invention it is important to observe the above given process conditions, which differ clearly from those of a drying process or a conventional baking process. As well in drying as also in baking the water contained in the moist mass is evaporated, so that a final product with a corresponding low remaining moisture content is obtained. Because of the higher temperatures used in baking the starch is degraded to a larger degree compared to in drying, whereby especially amylose and amylopectin are formed. In contrast thereto in the extrusion used according to the invention the water cannot escape can only partly escape at higher temperatures (so called cocking extrusion). Under these conditions (besides the temperature, the pressure is also substantially increased compared with a drying or baking process) the starch is degraded to a large extent, and especially dextrin is formed. It can be anticipated that for the success of the inventions besides the alternate recipe also these different process conditions are responsible.

At the extrusion a substantial reduction of the water content takes place, e.g. from 35 to about 10 to 20%. The drying to the final moisture content of ≤3.5% is obtained through heating up to 130° C. or through short time microwave treatment up to about 175° C. In the last case advantageously a further drying and careful cooling is performed in a following heating air tunnel until the product has the low temperature necessary for the packaging.

Because of the low moisture content the bars manufactured according to the invention are hygroscopic. Thus, it is advisable to pack the bars produced moisture-proof, e.g. by using suitable compound films with an aluminium layer as a water blocking layer. Compound films are available commercially, e.g. forms of paper/polyethylene/aluminium/polyethylene, polypropylene/aluminium/polyethylene or polyethyleneterephthalate/aluminium/polyethylene.

The examples given below serve for a more detailed explanation of the invention, the invention, however, not being limited thereto.

EXAMPLES

The following recipes were made:
Recipe A:

| Cholestyramine | 4000 mg (30% by weight) |
|---|---|
| wheat starch | 8600 mg (65% by weight) |
| wheat bran | 700 mg (5% by weight) |

For the manufacture of about 100 000 bars the mixture had the following composition:

| Cholestyramine | 400 kg |
|---|---|
| wheat starch | 860 kg |
| wheat bran | 70 kg |
| pur. water | 332.6 kg |
| dry aroma | 0,4 kg |

Recipe B:

| Cholestyramine | 4000 mg (25% by weight) |
|---|---|
| wheat starch | 10800 mg (67,5% by weight) |
| wheat bran | 1200 mg (7,5% by weight) |

Manufacturing process:

Firstly, cholestyramine, wheat starch, wheat bran as well as optional dry flavoring is mixed homogenously in an intense mixer.

Experiment 1 to 3

This mass was homogenized after the addition of the sufficient amount of water, extruded through a round die and formed into bars. The extrusion was performed with the aid of a single extruder screw. The control of the process parameters (temperature and pressure) was made according to a predetermined recipe (especially important are starch and water contents) through the selection of temperature as well as screw velocity, screw geometry and screw arrangement. The extruder used did have three heatable zones around the screw, which were heated through heating elements connected one after another. Firstly, the whole mass was compressed and kneaded at a rotational speed of 150 r.p.m., which led to a quick heating and melting of the mass. At about 170° C. temperature of the mass and a pressure of 50 bar (measured in the extruder head at a steady production phase) the soft, "gelatinized" mass became a viscous fluid. This was extruded through a circular nozzle. At the egress of the string from the nozzle the expansion phase of the mass began, whereby small, mainly open cells are formed through the escaping water vapor.

The pressure build-up in the extruder before the nozzle head depends on the temperature, the throughput and the nozzle geometry, whereby the pressure again is important for the forming and expansion conditions, respectively, of the mass after leaving through the nozzzle.

On the round string nozzle, which in the present case had a diameter of 5.0 mm, a diffusor nozzle was welded, in order to give the expanded material the desired flat bar form. A string with a width of 35 mm and a height of 10 mm was formed and divided into the desired length sections.

With the extruder used a mass throughput of about 10–11 kg/h was obtained. Pressure and temperature of the mass were measured at the extruder head. For recipes A and B the following process parameters were used:

| Experiment no | 1 | 2 | 3 |
|---|---|---|---|
| Recipe | A | A | B |
| Nozzle | 5.0 mm circular nozzle | 5.5 mm circular nozzle | 5.0 mm circular nozzle |
| Torque [Nm] | 243.1 ± 10.1 | 222.3 ± 16.3 | 245.4 ± 13.8 |
| R.p.m. | 151.2 ± 0,4 | 150.7 ± 0.3 | 150.7 ± 0.5 |
| Pressure [bar] | 49.4 ± 1.0 | 56.3 ± 5.5 | 49.4 ± 1.0 |
| Temp. [°C.] | 174.2 ± 0.4 | 168.4 ± 1.9 | 174.5 ± 1.7 |

The bars were subsequently post-dried in a drying plant (Hordentrockner) at 130° C. during 15–25 minutes to a remaining water content on average of 2.5 to 3.5% by weight. Through this post-drying a loose and crispy product is obtained and at the same time the remaining moisture content is reduced to below equilibrium moisture content, which prevents a microbiological destruction.

Experiment 4 and 5

The mass homogenized in the shearing mixer was extruded with the aid of a double screw extruder (Berstorff ZE 40A - 330; screw diameter 40 mm, screw length 1530 mm). This "cooking extruder" with double screw characteristics has the advantage that a further thorough mixing and contemporarily a reduced mechanical strain of the mass is obtained. The necessary amount of water would be supplied with the aid of a dosing pump after the first heating step in the extruder.

The extruder plant has 7 heating zones and a heatable head piece. The last heating zones were set at a temperature of 130° C., the head zone at a somewhat lower temperature. It was possible to cool the extruder by a water supply in order to guarantee an exact temperature control.

The crossing from the head piece to the forming nozzle was made through a bevelled slit nozzle (length 40 mm, height 10 mm). In the connected nozzle the slit tapered over a distance of 15 mm to 30 mm length and 6 mm height. The temperature of the mass and the pressure of the mass were registered at the extruder head and were recorded.

After leaving the nozzle the extruded material had a size of 40 mm width and 14 mm height. In the experiments the following process parameters were used.

| Experiment No | 4 | 5 |
|---|---|---|
| Recipe | B | B |
| Nozzle | slitnozzle 30 × 6 mm | slitnozzle 30 × 6 mm |

-continued

| Experiment No | 4 | 5 |
|---|---|---|
| r.p.m. | 170 | 170 |
| Temperature [°C.] | 111 | 115 |
| Pressure [bar] | 35–46 | 34–37 |

The extruded material was transferred to a cutting device with the aid of a conveyor. The drying was performed with the aid of a microwave dryer and a subsequent hot air tunnel. During the microwave treatment a temperature of 170° C. was reached for a short time and a remaining moisture content of about 5% was obtained. The object of the subsequent hot air tunnel was a further drying to a remaining moisture content of <3,5% and a cooling down to 80° C., in order to make possible the subsequent packaging.

In the experiments 1 to 5, bars having a width of 40 mm, a height of 6 mm and a length of 150 mm were manufactured. The bars had, when using a special dry aroma, such as of the type "bayrisches Gewürzbrot", a pleasant breadlike taste. It lacked the otherwise appearing unpleasant fishlike flavour and smell, and the bars did not show the feared drifting sand effect, i.e. there was no furry or sandy feeling in the mouth.

The ready, dried bars were packed in a moisture-proof compound sheeting of polyethylene terephalate/aluminium/polyethylene (HELIOnal® aluminum-combination foil), air and moisture-tight, which was necessary in view of the hygroscopic features of the products.

By grinding the extruded material and subsequent screening (≦2 mm) a composition in powder form was obtained, which like products existing on the market can be consumed in ample fluid or by addition to food-stuffs (such as milk or yogurt). The "drifting sand effect" does not occur here either, as has been shown through blind experiments with a patients collective.

We claim:

1. An oil-free composition containing cholestyramine and starch, preferably in the form of bars, especially for immediate consumption by hypercholesterolemia patients, obtainable by mixing cholestyramine and grain starch in a weight ratio of 1:1.8 to 2.9 with the addition of grain bran as a filler and optionally a flavoring with 10% to 35% by weight of water (relative to the starting materials) to a homogeneous moist mass, extruding to form the mass into a string, whereby the temperature is 105° to 180° C. (measured in the mass in the extruder head) and the pressure is 30 to 70 bars (measured in the extruder head), as well as subsequent drawing at a temperature exceeding 100° C. to a remaining moisture content of ≦3.5% by weight, as well as dividing the extruded material before or after the drawing into bars or grinding the extruded material into a powder.

2. A method of manufacturing cholestyramine- and starch-containing, oil-free compositions, preferably in the form of bars, especially for immediate consumption by hypercholesterolemia patients, which comprises the steps of mixing cholestyramine and grain starch in a weight ratio of 1:1.8 to 2.9 with the addition of grain bran as a filler and optionally a flavoring with 10% to 35% by weight of water (relative to the starting materials) into a homogeneous moist mass, forming of the mass through extrusion into a string, whereby the temperature is 105°–180° C. (measured in the mass in the extrusion head) and the pressure is 30–70 bars (measured in the extrusion head), and subsequently drying at a temperature above 100° C. to a remaining moisture content of ≦3.5% by weight, whereby the extruded material before or after the drying is divided into bars or is ground into a powder.

3. A method according to claim 2, wherein the starch and bran are from the same grain.

4. A method according to claim 2 or 3, wherein the starch is a wheat starch and the bran is a wheat bran.

5. A method according to claim 2 or 3, wherein up to 7.5% by weight of bran (relative to the starting materials) is added.

6. A method according to claim 2 or 3, wherein the drying is to a remaining moisture content of 2.5% to 3.5% by weight.

7. A method according to claim 2 or 3, wherein the flavoring is applied to the bar after the drying step.

8. A method according to claim 4, wherein up to 7.5% by weight of bran (relative to the starting materials) is added.

9. A method according to claim 4, wherein the drying is to a remaining moisture content of 2.5% to 3.5% by weight.

10. A method according to claim 4, wherein the flavoring is applied to the bar after the drying step.

11. A method according to claim 5, wherein the drying is to a remaining moisture content of 2.5% to 3.5% by weight.

12. A method according to claim 8, wherein the drying is to a remaining moisture content of 2.5% to 3.5% by weight.

* * * * *